United States Patent
Schneider-Nieskens

(10) Patent No.: US 7,122,054 B2
(45) Date of Patent: Oct. 17, 2006

(54) BREAST PROSTHESIS HAVING AN ADHESIVE LAYER

(75) Inventor: Reinhold Schneider-Nieskens, Celle (DE)

(73) Assignee: Thämert Orthopädische Hilfsmittel GmbH & Co. KG, Burgwedel (DE)

(*) Notice: Subject to any disclaimer, the term of this patent is extended or adjusted under 35 U.S.C. 154(b) by 37 days.

(21) Appl. No.: 10/683,754

(22) Filed: Oct. 10, 2003

(65) Prior Publication Data

US 2004/0073305 A1   Apr. 15, 2004

(30) Foreign Application Priority Data

Oct. 15, 2002  (DE)  ............ 202 15 801 U

(51) Int. Cl.
*A61F 2/52* (2006.01)
(52) U.S. Cl. .............................. 623/7; 623/8
(58) Field of Classification Search .......... 623/7, 623/8; 156/145, 245
See application file for complete search history.

(56) References Cited

U.S. PATENT DOCUMENTS

| 4,356,573 | A | 11/1982 | Knoche |
| 5,071,433 | A | 12/1991 | Naestoft et al. |
| 6,066,220 | A | 5/2000 | Schneider-Nieskens |
| 6,309,500 | B1* | 10/2001 | Jensen et al. ............ 156/247 |

FOREIGN PATENT DOCUMENTS

| DE | 27 42 394 | | 9/1977 |
| DE | 28 02 375 A1 | | 1/1978 |
| DE | G 92 03 947.2 | | 3/1992 |
| DE | G 93 06 572.8 | | 4/1993 |
| DE | 297 13 203 U1 | | 7/1997 |
| DE | 197 54 144 A1 | | 12/1997 |
| GB | 2 202 745 A | | 3/1987 |
| GB | 2270628 A | * | 3/1994 |
| WO | WO94/16650 | | 8/1994 |

\* cited by examiner

*Primary Examiner*—David J. Isabella
(74) *Attorney, Agent, or Firm*—Collard & Roe, P.C.

(57) ABSTRACT

A breast prosthesis has an adhesive element which forms a continuous surface conforming to the back section of the prosthesis which faces the user. One side of the adhesive element is detachably secured to the back section of the prosthesis and the other side of the adhesive element is detachably adhered to the user. The adhesive element is formed from an inner body which is lined with material. The breast prosthesis has a flat annular region on its back section and an elevated edge along the perimeter of the flat annular region. A gap is provided in the elevated edge at an upper region of the prosthesis. The adhesive element extends to the inner surface of the elevated edge and has a projection conforming to the gap.

7 Claims, 3 Drawing Sheets

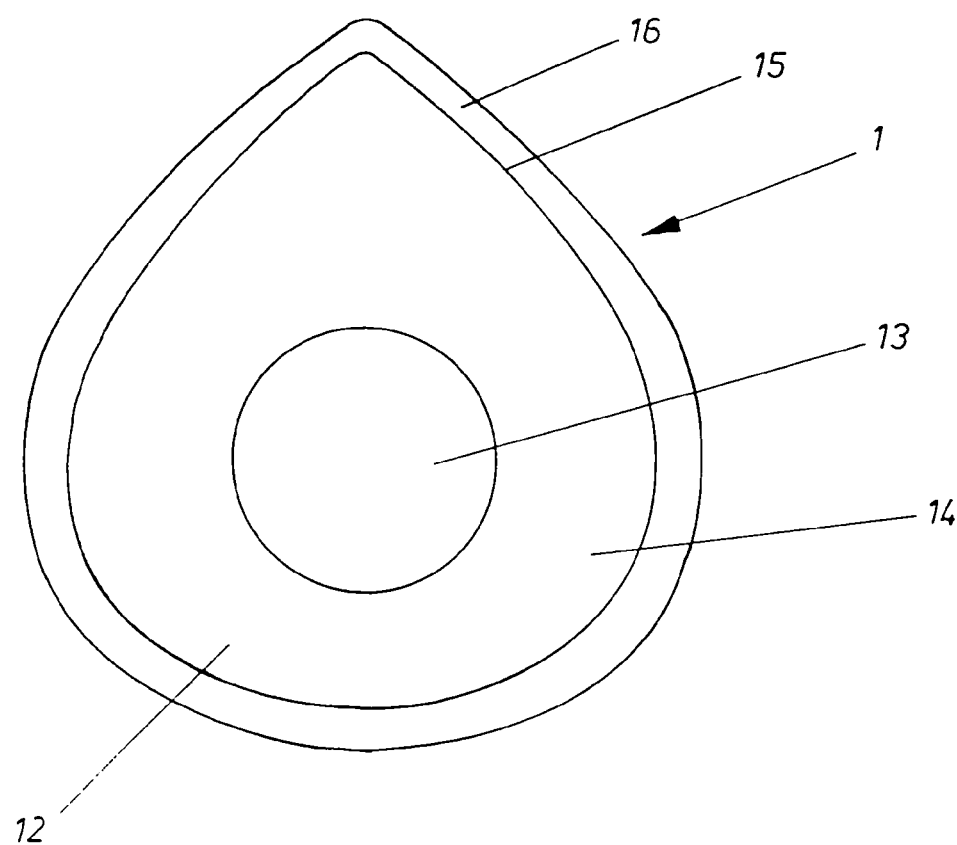
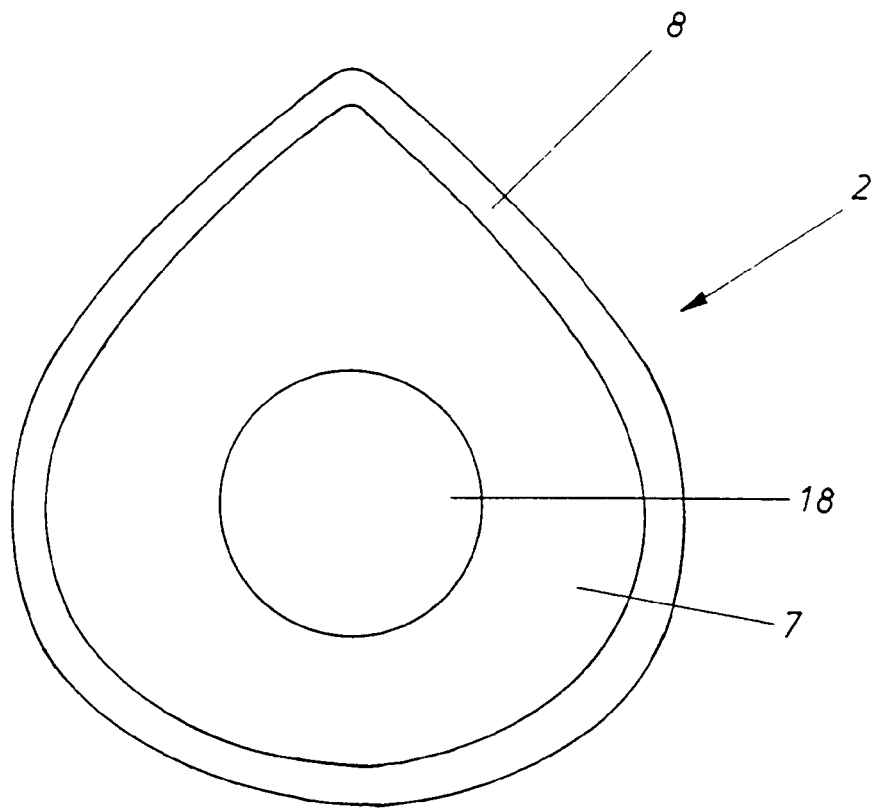

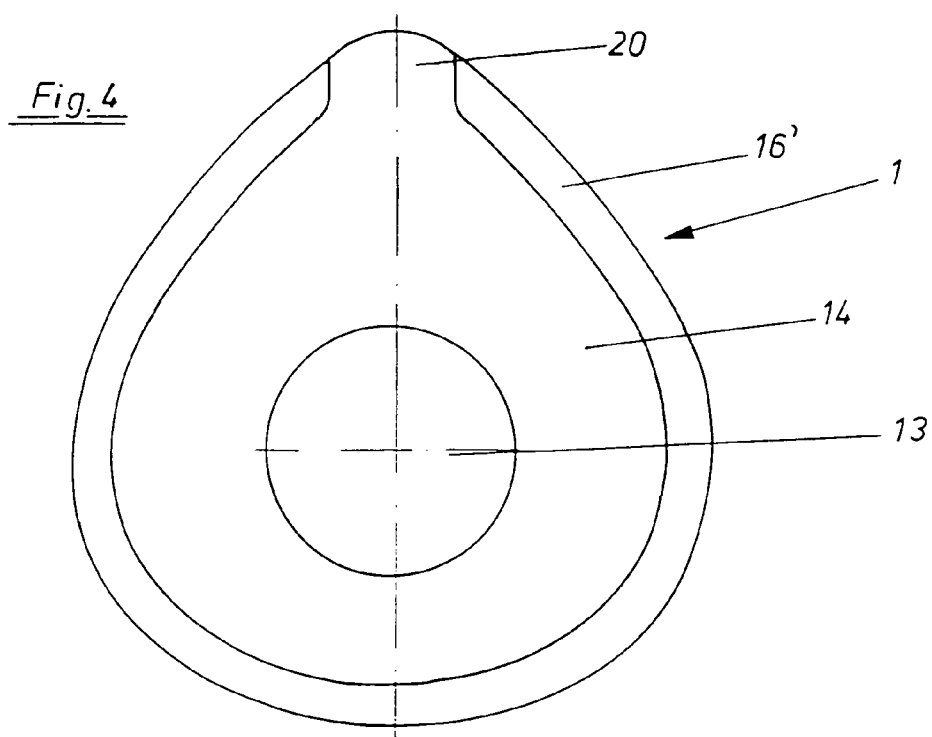
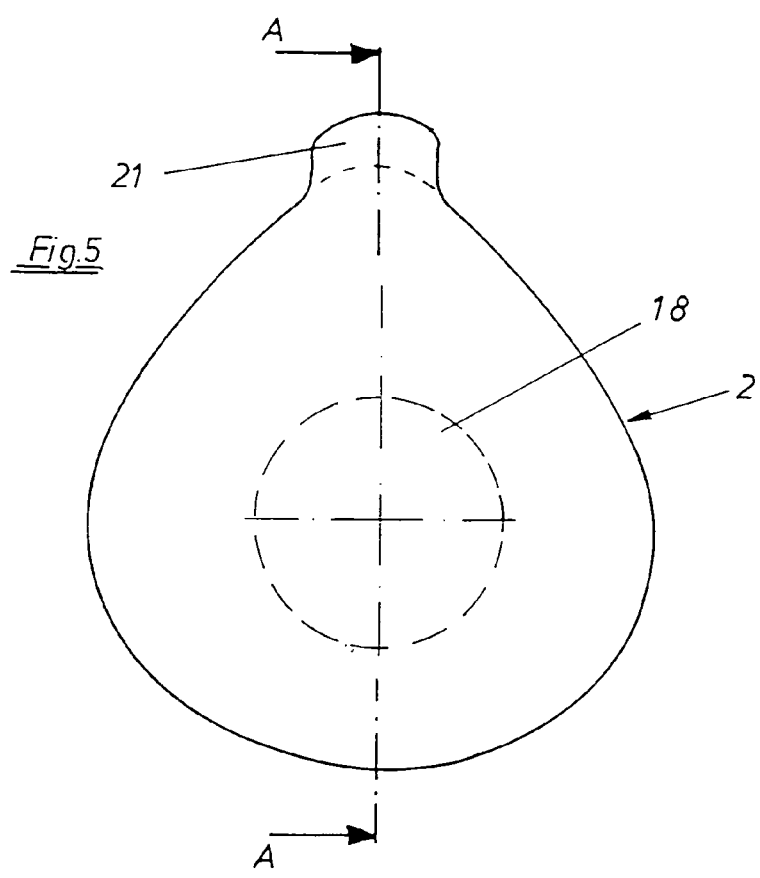
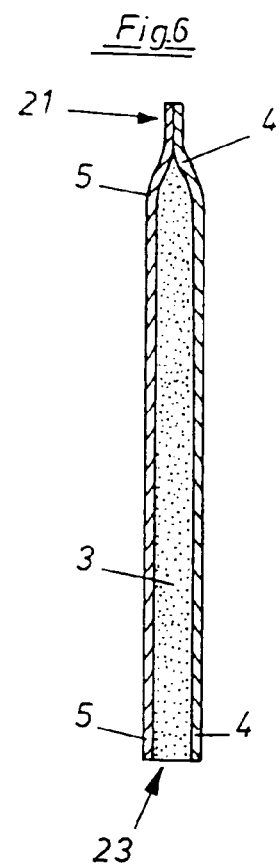

BREAST PROSTHESIS HAVING AN ADHESIVE LAYER

CROSS REFERENCE TO RELATED APPLICATIONS

Applicant claims priority under 35 U.S.C. §119 of German Application No. 202 15 801.2 filed Oct. 15, 2002.

BACKGROUND OF THE INVENTION

The present invention relates to a breast prosthesis having an adhesive element secured to the back of the breast prosthesis. The breast prosthesis is removably adhered to the skin of a user with such an adhesive element. Breast prostheses of this type are also referred to as adhesive prostheses.

Breast prostheses of this type having an adhesive element are problematic in that the manufacture of a permanent and reliably adhering adhesive element, which adheres even after multiple uses, is extremely difficult.

SUMMARY OF THE INVENTION

It is an object of the present invention to provide a breast prosthesis of the type described with a permanent, reliable adhesive element.

According to the present invention, a flat adhesive element is secured to the back of a breast prosthesis. The adhesive element is designed for detachable connection to the breast prosthesis on one side and for detachable adhesion to the skin of a user on the other side. In this way, the flat adhesive element, which may also be referred to as an adhesive pad, provides a type of adapter between the prosthesis and the body. Since the adhesive element is completely removable and therefore replaceable, the service life of the actual breast prosthesis is significantly extended. In addition, especially good fit and transition from the breast prosthesis to the body is achieved using the adhesive element, even in the case of shell-shaped, light prostheses.

The flat adhesive element may be coated on a side facing the body with an adhesive material, for example, adhesive silicone or an adhesive layer made of polyurethane or acrylates or other polymers. Adhesive silicones, which are used in the medical field, allow removable adhesion to the body and form a bond with the body which is harmless from a medical viewpoint. The flat adhesive element may preferably be coated with adhesive silicone on a side facing the breast prosthesis, so that adhesion also occurs on this side. In this case, the flat adhesive element is preferably coated with adhesive silicone on the entire surface of the adhesive element facing the user, including its border. By using the entire surface of the adhesive element as an adhesive region, an especially reliable bond is achieved. Providing an adhesive coating up to the edge can prevent the breast prosthesis from breaking away at its upper edge when it is under load. The adhesive element forms a continuous surface and its size and shape substantially conform to the back of the breast prosthesis. Accordingly, both sides of the flat adhesive element may be coated with adhesive silicone.

In an advantageous alternative embodiment, the side of the flat adhesive element facing the back of the breast prosthesis is provided with a hook-and-loop fastener. This may be either a loop felt or a hook element, which then interacts with a corresponding hook or loop element provided on the back of the breast prosthesis.

The flat adhesive element has an inner body which is lined with a material. This material is preferably an adhesive textile, such as terrycloth, on which adhesive materials may be reliably applied. The inner body is advantageously manufactured from a foam which is coated with a polyurethane. A flat adhesive element constructed in this manner is flexible, storable, and suitable for the application of a sticky adhesive silicone.

The breast prosthesis preferably consists of a light weight prosthesis. Such a prosthesis may be manufactured by mixing hollow microbeads into a gel, which leads to a reduction in weight. Additionally, the breast prosthesis is advantageously formed in a shell-shape. For example, the breast prosthesis has a recess or trough in the central region of the back of the prosthesis. This results in a reduction in weight and also improves the tailoring and deformation of the breast prosthesis.

An annular flat region may be provided on the back of the breast prosthesis. This region encloses the recess in the central region of the back of the breast prosthesis. The flat adhesive element is glued to this annular flat region, which is advantageously also coated with adhesive silicone. Due to the strong adhesive effect between the back of the breast prosthesis and the adhesive element, the non-sticky central shell-shaped region is much less annoying than if the breast prosthesis was glued directly to the skin.

Additionally, an edge may be provided on the back of the breast prosthesis along the outside perimeter of the annular flat region. This edge is elevated in relation to the annular flat region. The flat adhesive element is somewhat smaller than the breast prosthesis in this preferred embodiment, so that the flat adhesive element presses against the inside of the edge of the back of the breast prosthesis and in this way has its position aligned.

It is preferable to use a flat adhesive element which is exactly as large as the back of the breast prosthesis, with a region on the edge of the adhesive element which is somewhat thinner or tapered in relation to the central region of the adhesive element. Such an adhesive element forms an even, slightly concave surface on the side facing the user.

It is especially preferable to coat only the adhesive element with adhesive material and not to coat the breast prosthesis with adhesive material, so that the breast prosthesis may also be worn as a normal breast prosthesis. In principle, however, it is also possible to achieve a connection between the breast prosthesis and the adhesive element by applying adhesive material to the breast prosthesis or to the breast prosthesis and the side of the adhesive element facing toward the breast prosthesis.

In addition to the advantage of the replaceability of the adhesive element, the shell-shaped breast prosthesis, according to the present invention, may be used anywhere and an adapter may be provided for tailoring and/or compensating for the trough-shaped shell. The light prosthesis is preferably formed from a gel body interspersed with hollow microbeads, and coated with a silicone cover layer. This embodiment of a light prosthesis is also comparatively stable and is especially suitable for use with the adhesive element.

In another preferred embodiment of the present invention, the back of the breast prosthesis or side of the breast prosthesis facing toward the user has a peripheral edge or elevated border. The adhesive element in this embodiment is somewhat smaller than the back of the breast prosthesis and presses against the inside of the border of the breast prosthesis, that is, it may be inserted into the area enclosed by the border. For this embodiment, the edge or border is preferably not formed as completely continuous, but rather has a gap or recess in the vicinity of the upper portion of the breast prosthesis. A projection corresponding to the gap or recess is provided in the adhesive element, so that in the region of the upper tip of the breast prosthesis, the adhesive element extends directly up to or up to 2 mm onto the border of the breast prosthesis. This provides especially strong and reliable adhesion, particularly in the region of the upper tip, which may otherwise easily break away if the border is loaded.

BRIEF DESCRIPTION OF THE DRAWINGS

Other objects and features of the present invention will become apparent from the following detailed description considered in connection with the accompanying drawings which disclose several embodiments of the present invention. It should be understood, however, that these drawings are designed for the purpose of illustration only and not as a definition of the limits of the invention In the drawings, wherein similar reference characters denote similar elements throughout the several views:

FIG. 2 shows a top view of the back of the breast prosthesis;

FIG. 3 shows a top view of the side of the adhesive element facing the back of the breast prosthesis;

FIG. 4 shows a top view of the back of a second embodiment of a breast prosthesis according to the present invention;

FIG. 5 shows a top view of the side of the adhesive element of a second embodiment of the present invention facing the back of the breast prosthesis; and FIG. 6 shows a sectional side view of the adhesive element along line A—A in FIG. 5.

DETAILED DESCRIPTION OF THE INVENTION

Figure 1:
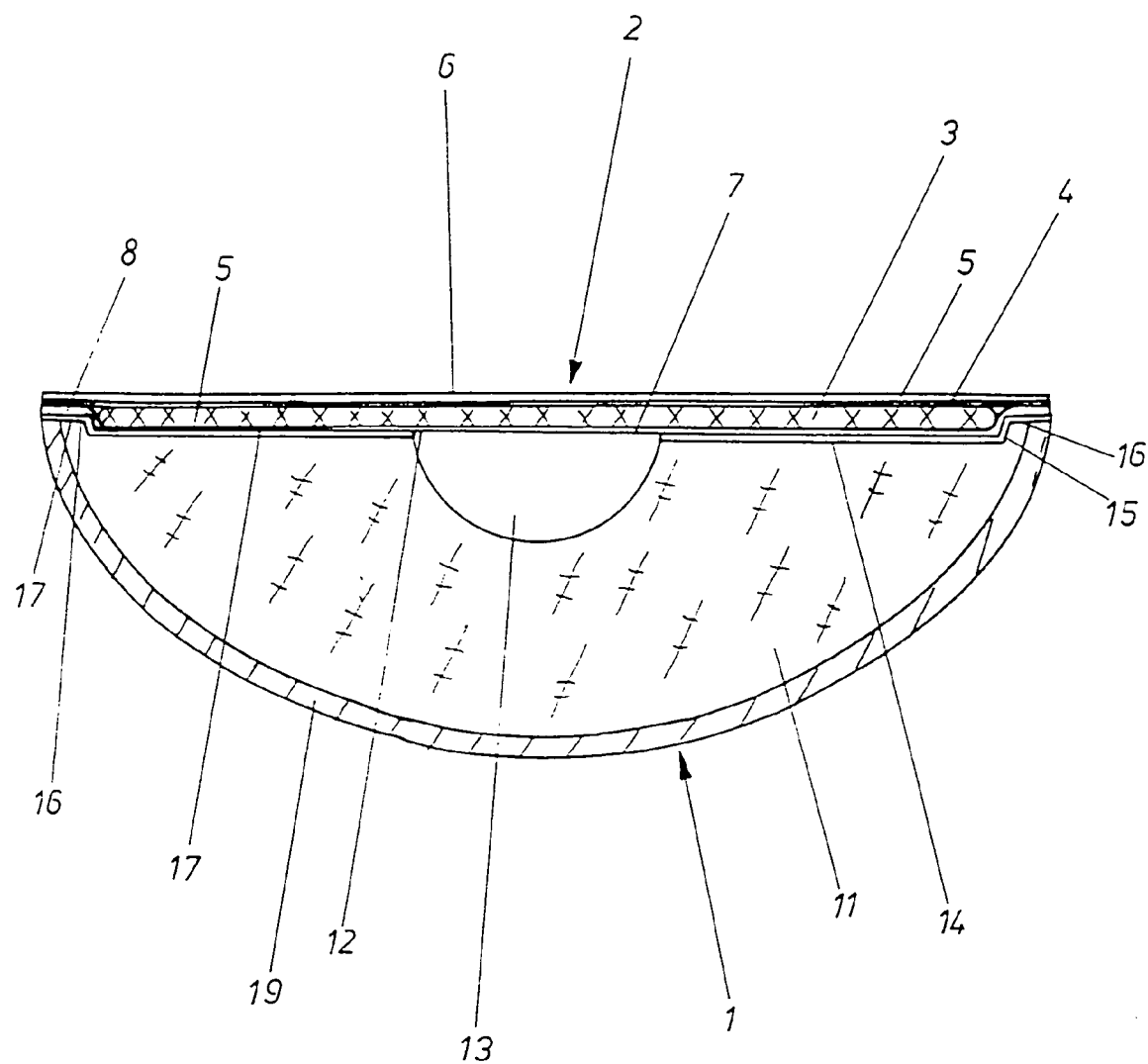
FIG. 1 shows a sectional side view of a breast prosthesis and an adhesive element.

Turning now in detail to the drawings, FIG. 1 shows a cross-sectional view through breast prosthesis 1 with an adhesive element 2 glued thereon. The breast prosthesis 1 is primarily formed by a gel body 11. This gel body is coated with a silicone cover layer 19, as is described in German Patent Application 197 54 144 A1. The gel body 11 is made of light silicone and hollow microbeads.

The back 12 of breast prosthesis 1, which faces toward the user, has a recess 13 in its central region, which provides the breast prosthesis 1 with a shell-shape and also contributes to the light weight character of the prosthesis.

A flat region 14, delimited in a border region by a nearly vertical section 15, which is approximately 2 mm to 3 mm high, is provided around the recess 13. An essentially horizontal edge 16, which is slanted slightly toward gel body 11, adjoins vertical section 15. The flat region 14, the vertical section 15, and the edge 16 are coated with adhesive silicone 17. The flat adhesive element 2 is glued to the back 12 of breast prosthesis 1. The adhesive element has a side 7 facing toward the breast prosthesis 1 and a side 6 facing toward the user. The shape and dimensions of the adhesive element 2 are essentially determined by a foam element 3, which is coated with polyurethane and lined with a textile 4, for example, terrycloth. This textile 4 is impregnated or coated with adhesive silicone 5, which adheres to the skin of the wearer on a side 6 facing the wearer and to the adhesive silicone layer 17 provided in the flat region 14 and the border regions 15 and 16 of the breast prosthesis 1 on the side 7 of the adhesive element facing the back of the breast prosthesis.

There is no stiffening foam 3 in the border regions, so that the entire adhesive element 2 tapers in the border region 8 and thus compensates for the geometry of the breast prosthesis in the region of the edge 16, so that a slightly concave continuous surface is formed overall on the side 6 of the adhesive element facing toward the wearer. Precise and form-fitting alignment of the adhesive element 2 with the breast prosthesis 1 is made possible by including edge 16 in the border region of breast prosthesis 1.

FIG. 2 shows a top view of the back 12 of the breast prosthesis 1. A recess 13 is provided in a central region of the breast prosthesis 1, which is particularly used to save weight. A flat region 14 is provided around recess 13. A vertical section 15, already described in FIG. 1, adjoins flat region 14 on the outside, which adjoins nearly horizontal edge 16, having a width of approximately 1 cm. Both flat region 14 and vertical section 15, as well as edge 16, are preferably coated with adhesive silicone. Recess 13 is preferably not coated with adhesive silicone.

FIG. 3 shows a top view of the adhesive element 2 from the side 7 facing toward breast prosthesis 1. The adhesive element 2 is essentially flat in this embodiment, and the border region 8 of adhesive element 2 is offset to the rear or thinner in relation to the rest of the adhesive element, so that it is tailored to the projecting border of the breast prosthesis 1. The adhesive element 2 is coated with an adhesive material, for example, adhesive silicone. The portion of the adhesive element on the side facing toward the prosthesis which corresponds to the recess or depression in the prosthesis is not coated with adhesive material or, after an initial complete coating with adhesive material, is covered with a film so that recess 13 of breast prosthesis 1 does not adhere to adhesive element 2. This region, which is not coated or is coated and subsequently covered with a film, is indicated in FIG. 3 by 18.

A second embodiment of the breast prosthesis according to the present invention is illustrated in FIGS. 4, 5, and 6.

FIG. 4, similarly to FIG. 2, shows a top view of the back of breast prosthesis 1. In this embodiment as well, a recess 13 is provided in the central region of breast prosthesis 1, which is particularly used to save weight. A flat region 14 is provided around recess 13. The essential difference from the embodiment first described is edge 16', which does not extend around the entire circumference of breast prosthesis 1, but has a gap or recess 20 in an upper region of the breast prosthesis, in which flat region 14 continues.

FIG. 5, similarly to FIG. 3, shows a top view of the side of the adhesive element which faces the back of the breast prosthesis. The outer circumference of adhesive element 2 around the region of edge 16' is smaller than that of adhesive element 2 shown in FIG. 3, since in this embodiment adhesive element 2 is formed in such a way that it rests on flat region 14 completely within edge 16'. In this embodiment, edge 16' of the prosthesis rests on the skin of the user, rather than adhering to the adhesive element, as in the first embodiment.

The gap or recess 20 in edge 16' at the upper tip region of prosthesis 1 is especially important for gluing, since the edge may break away here in the event of loading. Adhesive element 2 has a projection or offshoot 21 here, whose size is tailored to the gap or recess 20 in the edge 16'. The offshoot extends up to approximately 2 mm on the edge.

FIG. 6 shows a section along the line A—A in FIG. 5. The construction of adhesive element 2 is similar to the construction shown in FIG. 1. The essential difference is that adhesive element 2 illustrated in FIG. 6 has a straight termination edge 23 in an outer region, which abuts the inside of edge 16'. The adhesive element 2 shown in FIG. 6 tapers to a narrow element, made of adhesive silicone and textile, only in the region of offshoot 21. The foam core 3 does not extend into offshoot 21.

Accordingly, while a few embodiments of the present invention have been shown and described, it is to be understood that many changes and modifications may be made thereunto without departing from the spirit and scope of the invention as defined in the appended claims.

What is claimed:

1. A breast prosthesis comprising:
   a back section adapted for facing a user;
   an annular flat region located on said back section;
   an edge extending along an outside perimeter of said annular flat region and having a gap located in an upper region of said breast prosthesis; wherein said edge is elevated in relation to said annular flat region; and
   an adhesive element forming a continuous surface substantially conforming to said annular flat region and extending to an inner surface of said edge, having a projection conforming to said gap;
   wherein a side of said adhesive element facing said breast prosthesis is detachably secured to said annular flat region and a side of said adhesive element adapted for facing a user is detachably adherable to said user.

2. The breast prosthesis according to claim 1, wherein said adhesive element is coated with an adhesive material.

3. The breast prosthesis according to claim 2, wherein said adhesive material is adhesive silicone.

4. The breast prosthesis according to claim 2, wherein said adhesive element is coated with said adhesive material on an entire surface of said adhesive element on at least said side of said adhesive element adapted for facing a user.

5. The breast prosthesis according to claim 1, wherein said side of said adhesive element facing said breast prosthesis is detachably secured to said back section of said breast prosthesis with hook and loop fasteners.

6. The breast prosthesis according to claim 1, wherein said breast prosthesis is shell-shaped.

7. The breast prosthesis according to claim 1, wherein said breast prosthesis comprises a light weight prosthesis.

* * * * *